United States Patent [19]

Illian et al.

[11] Patent Number: 5,370,823
[45] Date of Patent: Dec. 6, 1994

[54] PYRIMIDINECYCLOHEXANE DERIVATIVES, PROCESS FOR THEIR PREPARATION, AND THEIR USE IN LIQUID-CRYSTALLINE MIXTURES

[75] Inventors: Gerhard Illian, Frankfurt am Main; Wolfgang Hemmerling, Sulzbach/Taunus; Rainer Wingen, Hattersheim am Main, all of Germany

[73] Assignee: Hoechst Aktiengesellschaft, Frankfurt am Main, Germany

[21] Appl. No.: 924,058

[22] PCT Filed: Dec. 13, 1991

[86] PCT No.: PCT/EP91/02400

§ 371 Date: Sep. 3, 1992

§ 102(e) Date: Sep. 3, 1992

[87] PCT Pub. No.: WO92/12218

PCT Pub. Date: Jul. 23, 1992

[30] Foreign Application Priority Data

Jan. 5, 1991 [DE] Germany ............... 4100176

[51] Int. Cl.$^5$ ............... C09K 19/34; C09K 19/52; C07D 239/02
[52] U.S. Cl. ............... 252/299.610; 252/299.01; 544/295; 544/296; 544/298
[58] Field of Search ............... 252/299.61; 544/298, 544/295, 296, 299.01

[56] References Cited

U.S. PATENT DOCUMENTS 4,609,485  9/1986  Kitano et al. ............ 252/299.61
4,640,796  2/1987  Yoshida et al. ............ 252/299.61

FOREIGN PATENT DOCUMENTS 0186045  12/1985  European Pat. Off. .
60-193969  10/1985  Japan .

*Primary Examiner*—Robert L. Stoll
*Assistant Examiner*—C. Harris
*Attorney, Agent, or Firm*—Curtis, Morris & Safford

[57] ABSTRACT

A liquid-crystalline bispyrimidinylcyclohexane of the formula (I)

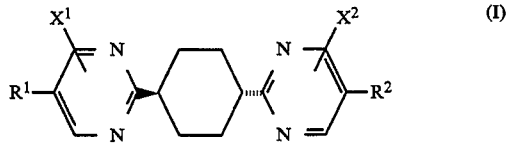

in which:
$R^1$ and $R^2$ are identical or different and are, for example, straight-chain or branched alkyl,
$X^1$ and $X^2$ are identical or different and are H, F, Cl or CN, is particularly suitable as a component of liquid-crystal mixtures.

In nematic and smectic liquid-crystal mixtures, these compounds result in low melting points and broad phase ranges.

10 Claims, No Drawings

PYRIMIDINECYCLOHEXANE DERIVATIVES, PROCESS FOR THEIR PREPARATION, AND THEIR USE IN LIQUID-CRYSTALLINE MIXTURES

The unusual combination of anisotropic and fluid behavior of the liquid crystals has resulted in their use in electro-optical switching and display devices, where their electrical, magnetic, elastic and/or thermal properties can be utilized to cause changes in alignment. Optical effects can be achieved, for example, with the aid of birefringence, inclusion of dichroically absorbent dye molecules ("guest-host mode") or light scattering.

In order to satisfy the ever increasing demands of practice in the various areas of application, there is a constant demand for novel improved liquid crystal mixtures and thus also for a large number of mesogenic compounds of various structure. This applies both to the areas in which nematic LC phases (for example TN="twisted nematic", STN="supertwisted nematic", SBE="supertwisted birefringence effect", ECB ="electrically controlled birefringence") are used, and to those having smectic LC phases (for example ferroelectric and electroclinic).

Many of the compounds which are suitable for LC mixtures can be described by a structure principle [see, for example, J. Am. Chem. Soc. 108, 4736 (1986), Structure I; Science 231, 350 (1986), FIG. 1 A; J. Am. Chem. Soc. 108, 5210 (1986), FIG. 3], in which the rings from cyclic compounds - aromatic compounds, heteroaromatic compounds, but also saturated ring systems - are linked to straight-chain alkyl side chains or to alkyl side chains which are substituted in the chain by small groups (for example methyl or chlorine) and are thus branched. The object of the present invention is to provide novel mesogenic bispyrimidinylcyclohexane compounds which can be combined with other components to give novel LC mixtures which have particularly advantageous properties for practical use. The liquid-crystalline bispyrimidinylcyclohexane compounds of the formula (I) defined below achieve this object,

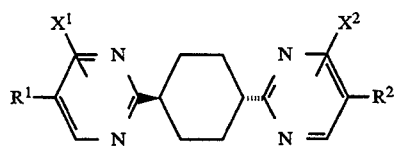

where $R^1$ and $R^2$ are identical or different straight-chain or branched (with or without an asymmetric carbon atom) alkyl or alkenyl having 1 to 16 carbon atoms, it also being possible for one or two non-adjacent —$CH_2$— groups to be replaced by —O—, —S—, —CO—, —CO—O—, —O—CO— or —O—CO—O, and it also being possible for one or more H to be replaced by F, or are one of the following radicals: $OCF_3$, $OCHF_2$,

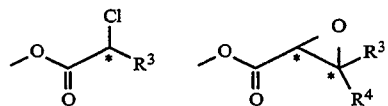

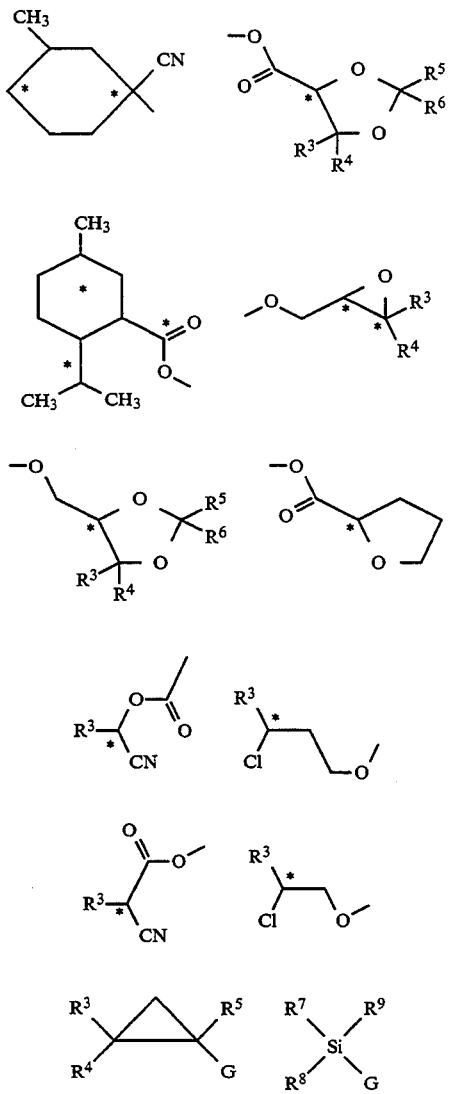

$X^1$ and $X^2$ are identical or different H, F, Cl, CN, preferably H or F, $R^3$, $R^4$, $R^5$ and $R^6$ are identical or different H, straight-chain or branched alkyl having 1 to 16 carbon atoms or alkenyl having 2–16 carbon atoms, in which, in addition, one —$CH_2$— group may be replaced by —O—, —CO—O— or —O—CO—, or $R^3$ and $R^4$ or $R^5$ and $R^6$ together are cyclic alkyl having 3-8 carbon atoms, $R^7$, $R^8$ and $R^9$ are identical or different straight-chain or branched alkyl having 1 to 16 carbon atoms or alkenyl having 2 to 16 carbon atoms, in which, in addition, one or two non-adjacent —$CH_2$— groups may be replaced by —O—, —CO—O— or —O—CO—, with the proviso that silicon is only bonded to one or more carbon atoms which have H and/or C as neighboring atoms, or are cyclic alkyl having 3 to 8 carbon atoms, or, together with the Si atom, are alternatively

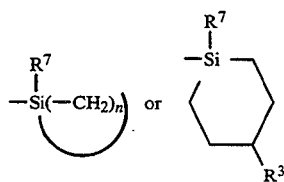

G is straight-chain or branched alkylene having 1 to 16 carbon atoms or alkenylene having 2 to 16 carbon atoms, in which, in addition, one or two non-adjacent —CH$_2$— groups may be replaced by —O—, —S—, —O—CO—, —CO—O—, —S—CO— or —CO—S—, with the proviso that Si is only bonded to a carbon atom which has H and/or C atoms as neighboring atoms, n is 3 to 8.

Preference is given to compounds in which $R^1$ and $R^2$ are both linear or branched alkyl having 1 to 16 carbon atoms or alkoxy having 1 to 15 carbon atoms or alkyldimethylsilylalkyl(oxy) of the formula $R^7$—Si(CH$_3$)$_2$—G. Preference is furthermore given to compounds in which $R^1$ is linear or branched alkyl or alkoxy, and $R^2$ is one of the abovementioned optically active substituents. Preference is also given to compounds of the formula (I) in which $R^1$ and $R^2$ are identical and to compounds in which $X^1 = X^2 = H$ or $X^1 = X^2 = F$.

The compounds according to the invention are distinguished, inter alia, by the fact that they have a broad nematic phase. This property makes these compounds particularly suitable for raising the clearing point and depressing the melting point in nematic and ferroelectric mixtures. In addition, these compounds are particularly suitable for optimizing the effective switching angle in ferroelectric liquid-crystal mixtures.

The present invention furthermore relates to a liquid-crystal mixture (having a nematic, chiralnematic, smectic, chiralsmectic and/or ferroelectric phase) comprising at least two components - generally comprising 2 to 20 components - and containing at least one compound of the formula (I). The further components may in principle be any known mesogenic compounds (such as, for example, phenyl benzoates, biphenyls or phenylpyrimidines). In general, the mixture according to the invention contains from 0.1 to 90 mol%, in particular from 1 to 60 mol%, of pyrimidinylcyclohexane derivatives of the formula (I).

The invention furthermore relates to a liquid-crystal switching and display device (containing the conventional components, such as outer plates, liquid-crystal medium, alignment layer, electrodes, polarizers, etc.) in which the liquid-crystal medium contains at least one compound of the formula (I).

The compounds according to the invention can be prepared by known standard reactions from trans-cyclohexanedicarboxylic acid, for example by the route given in the scheme:

Scheme I

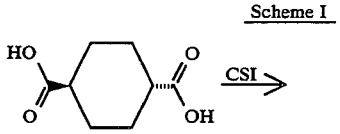

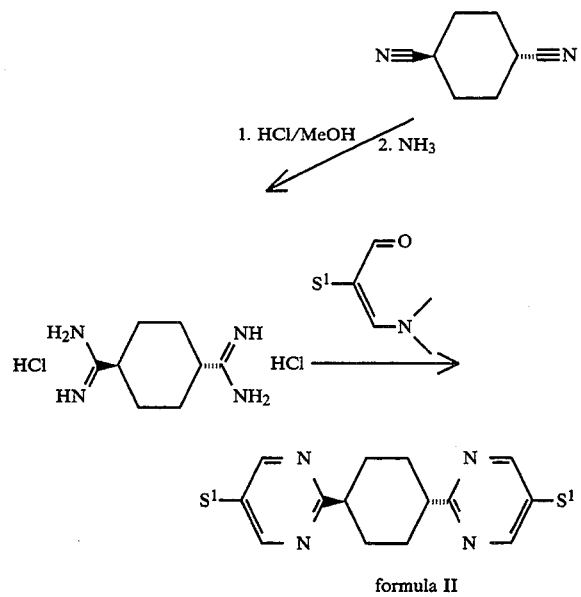

formula II $S^1$ is identical to $R^1$ or corresponds to a protecting group, such as benzyloxy, trialkylsilyloxy, tetrahydropyranyloxy, acyloxy or benzylthio.

The synthesis proceeds from trans-cyclohexane-1,4-dicarboxylic acid, which is converted into the transdinitrile using, for example, chlorosulfonyl isocyanate by the method of G. Lohaus (Org. Synth. Coll. Vol. VI, 304 (1988)). Transformation of the dinitrile into the diamidine and reaction with a dimethylaminoacrolein is carried out analogously, for example, to the method of H. Schubert and H. Zaschke (J. Prakt. Chem. 312, 494 (1970)).

Asymmetrical compounds of the formula I can be synthesized by methods known from the literature by first converting ethyl trans-4-cyanocyclohexane-1-carboxylate into trans-4-(pyrimidin-2-yl)cyclohexanecarboxyamide via a monoamidine. Transformation of the amide group of this amide into the amidine and reaction with a further dimethylaminoacrolein or an equivalent C$_3$ unit gives the desired product (see Shceme II), Scheme II

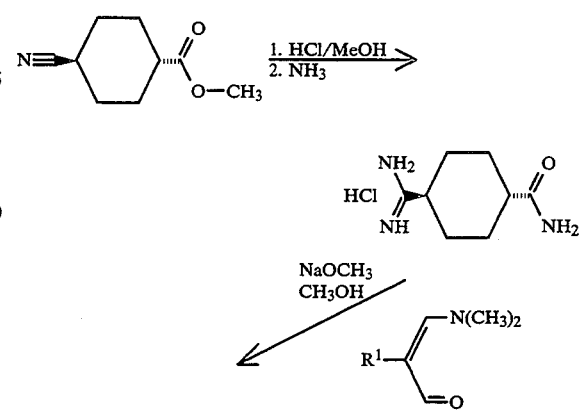

-continued
Scheme II

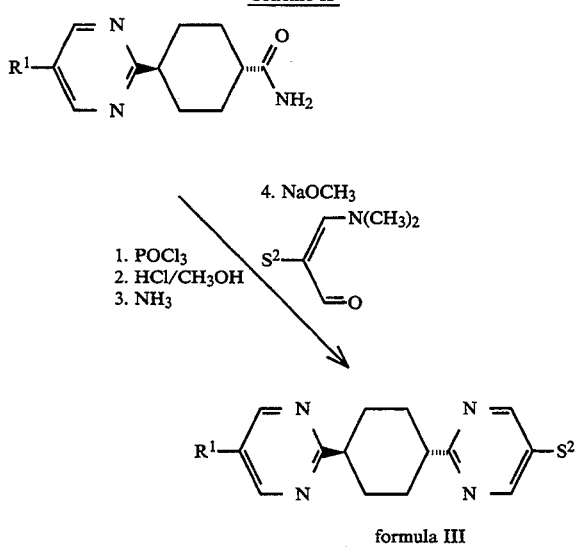

formula III where $S^2$ is identical to $R^2$ ($R^2$ is different from $R^1$) or is a protecting group, such as benzyloxy, trialkylsilyloxy, tetrahydropyranyloxy, acyloxy, benzylthio or another protecting group which is suitable for phenols, as mentioned in T. W. Greene (Protective Groups in Organic Synthesis, Wiley (1981)). The protecting groups can be removed by the methods recommended in the same reference.

Compounds of the formula (IV) where $X^{\frac{1}{2}}$ is F or Cl can be synthesized in the following way (see Scheme III),

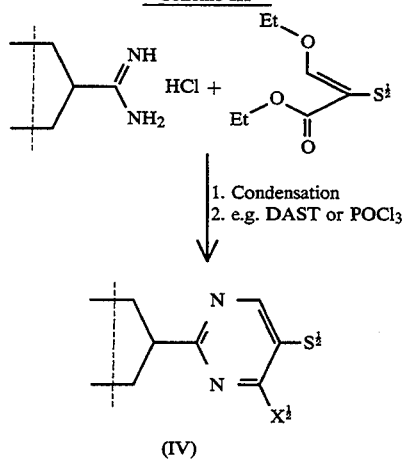

by condensing a suitable amidine with a 2-ethoxymethylenecarboxylic acid ester derivative, for example by the method of A. Boiler et al. (Z. Naturforsch. 33b, 433–438 (1978)). The 4-hydroxy group on the pyrimidine ring can then be replaced by chlorine or fluorine using $POCl_3$ or diethylaminosulfur trifluoride (DAST) respectively. In order to obtain compounds in which $X^{\frac{1}{2}}$ is CN, the compound where $X^{\frac{1}{2}}$ is Br, which is prepared analogously to the chlorine compound, is reacted with copper cyanide in a suitable solvent, such as N-methylpyrrolidone.

Ethers of the formula I can be prepared, if the ether structure was not already present before the formation of the heterocyclic compounds, from phenols of the formula II, III or IV where $S^1$ or $S^2$ is OH or O-(alkali) by reaction with monofunctionally reactive alkyl or alkenyl halides, or from monofunctionally reactive alcohols—as can be derived from the radicals listed under $R^1$—or the mesylates or tosylates thereof, the synthesis of these reaction components being known.

Thus, for example, phenol or thiophenols of the formula II, III or IV can be linked to hydroxyl compounds in the presence of triphenylphosphine/azodicarboxylic acid diesters (Mitsunobu reaction, for example in J. Chem. Soc. Perkin Trans 1, 1975, 461).

It is also possible to react the alkali metal or alkaline earth metal salts of these mesogenic hydroxyl or mercapto compounds, produced separately or as intermediates, with halogen compounds, toluenesulfonyloxy compounds or methylsulfonyloxy compounds (Williamson reaction, for example in Patai, The Chemistry of the Ether Linkage, Interscience Publishers, New York 1967, S. 446–468).

Phenols or thiophenols of the formula II, III or IV can also be reacted with carboxylic acids, as can be derived from $R^1$ under condensation conditions (for example March Advanced Organic Chemistry, 3rd Ed., Wiley-Interscience, New York, 1985, p. 240, 348–353) or under the conditions of the Williamson reaction to give esters or thioesters. In the same way, this is also possible with mesogenic carboxylic acids ($S^1/S^2$ =COOH) and the hydroxyl compounds derived from $R^1$.

The values for the spontaneous polarization $P_s$ [$nC/cm^2$], the optical response time $\tau$ [$\mu S$] and the effective switching angle $\theta_{off}$ [°] were determined as follows for the ready-to-use ferroelectric liquid-crystalline mixtures:

The $P_2$ values are measured by the method of H. Diamant et al. (Rev. Sci. Instr. 28, 30 (1957)), in which measurement cells having an electrode separation of 2 $\mu m$ and containing rubbed polyimide as the alignment layer are used. In order to determine $\tau$ and $\theta_{off}$, the measurement cell is mounted on the rotating stage of a polarizing microscope between analyzer and polarizer. By rotating the stage, the position of the stage for minimum light transmission is determined for the two switching states in the cell. The difference between the two positions on the rotating stage is equal to twice the effective tilt angle.

The response time $\tau$ is determined with the aid of a photodiode by measuring the time taken for the light signal to rise from a signal height of 10% to 90%. The switching voltage comprises rectangular pulses and is $\pm 10$ V/$\mu m$. The phase transition temperatures are determined with the aid of a polarizing microscope from the changes in texture on heating. By contrast, the melting point was determined using a DSC instrument. The phase transition temperatures between the phases nematic (N or N*)
smectic C ($S_C$ or $S_C$*)
smectic A ($S_A$ or $S_A$*)
crystalline (X or K)

are given in °C, and the values are between the phase designations in the phase sequence.

EXAMPLE 1

Synthesis of trans-1,4-bis(5-octyloxypyrimidin-2-yl)cyclohexane

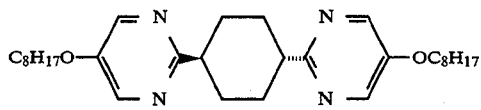

50.4 g (357 mmol) of chlorosulfonyl isocyanate in 30 ml of dichloromethane are added dropwise to 30 g (174 mmol) of trans-cyclohexane-1,4-dicarboxylic acid in 90 ml of dichloromethane under reflux. When the evolution of gas is completed, the mixture is stirred for a further 1.5 hours under reflux. 40 ml (715 mmol) of DMF are subsequently added dropwise at from −15 to −20° C., and the mixture is stirred for a further 15 minutes and hydrolyzed using 300 ml of ice water. The phases are separated, and the aqueous phase is extracted with dichloromethane. The combined organic phases are washed four times with water, dried over $MgSO_4$ and evaporated in vacuo. Crystallization from DMF gives 8.74 g (37.4%) of trans-cyclohexane-1,4-dinitrile.

Hydrogen chloride is added to 6.71 g (50 mmol) of transcyclohexane-1,4-dinitrile in 6.41 g (200 mmol) of absolute methanol and 100 ml of dioxane at 0° C until the mixture is saturated. The mixture is then stirred at 0° C. for 15 hours. The precipitated product is filtered off with suction under nitrogen, washed with dioxane and dried at 50° C. in vacuo over KOH.

The 10.05 g (37.1mmol=74% yield) of trans-cyclohexane-1,4-diiminomethyl ester dihydrochloride obtained are dissolved in 112 ml of ethanol, and 81.5 ml of saturated ethanolic ammonia solution are added. The mixture is stirred at 60° C for 2.5 hours and at room temperature for 15 hours. The mixture is then evaporated almost to dryness and stirred with ether, and the resulting precipitate is filtered off with suction. Drying in vacuo gives 8.45 g (94.5%) of trans-cyclohexane-1,4-diamidine dihydrochloride.

2.27 g (9.96 mmol) of 2-octyloxy-3-dimethylaminoacrolein in 5 ml of ethanol and 1.0 g (4.15 mmol) of transcyclohexane-1,4-diamidine dihydrochloride are added dropwise at room temperature to 230 mg (9.96 mmol) of sodium, dissolved in 6.3 ml of ethanol, and the mixture is refluxed for 120 hours. After cooling, the reaction solution is adjusted to pH 3 using semiconcentrated HCl and evaporated, and 30 ml of water are added to the residue. The aqueous solution is extracted several times with dichloromethane. The organic phases are combined, dried over magnesium sulfate and evaporated in vacuo. Chromatographic purification on silica gel and crystallization from hexane gives 380 mg (18%) of the end product. The product has the following phase sequence:

X 48 $S_x$ 114.8 N 135 I

EXAMPLE 2

Preparation of a mixture

A mixture comprising 60 mol% of the compound in example 1 and 40 mol% of the compound 4-ethyl-2-fluoro-4'-[2-(trans-4-n-pentylcyclohexyl)ethyl]biphenyl (component B) is prepared.

This has a clearing point of 111° C. Compared with the pure component B (phase sequence B: X 24 $S_B$ (13) N 103.4 I), the clearing point is significantly increased in this mixture by the addition of the compound according to the invention.

EXAMPLE 3

Use in mixture a) A mixture comprising the components (in mol%)

| | |
|---|---|
| 5-octyloxy-2-(4-hexyloxyphenyl)pyrimidine | 8.1 |
| 5-octyloxy-2-(4-butyloxyphenyl)pyrimidine | 8.6 |
| 5-octyloxy-2-(4-decyloxyphenyl)pyrimidine | 6.8 |
| 5-octyloxy-2-(4-octyloxyphenyl)pyrimidine | 3.7 |
| 5-octyl-2-(4-hexyloxyphenyl)pyrimidine | 12.8 |
| 5-octyl-2-(4-octyloxyphenyl)pyrimidine | 11.5 |
| 5-octyl-2-(4-decyloxyphenyl)pyrimidine | 8.7 |
| 4-(5-dodecylpyrimidin-2-yl)phenyl trans-4-pentylcyclohexanecarboxylate | 12.6 |
| 5-pentyl-2-(-4-cyanophenyl)pyrimidine | 2.0 |
| (2S, 3S)-2-(4-(5-octylpyrimidin-2-yl-)phenyloxy)methyl-3-butyloxirane | 5.7 |
| (4-(2-octyloxypyrimidin-5-yl)phenyl (2R, 3R)-3-propyl-oxirane-2-carboxylate | 6.4 |
| (S)-4-(2-octyloxypyrimidin-5-yl)phenyl (spiro(1,3-dioxolano-2,1'-cyclohexane)-4-yl)methyl ether | 3.3 |
| trans-1,4-bis(5-octyloxypyrimidin-2-yl)-cyclohexane | 9.8 | has the following liquid-crystalline phase ranges:

X -7 $S_c^*$ 49 $S_A^*$ 58 N* 85 I and has a spontaneous polymerization at 25° C. of 17.5 in the $nC/cm^2$.

EXAMPLE 4

Structure of a switching and display device

The ferroelectric mixture from example 3 is introduced into a polyimide-coated cell with a thickness of 2 μm (manufacturer EHC, Tokyo, Japan) and treated for 10 minutes with a rectangular field of 15 $V/cm^2$ and a frequency of 10 Hz. The FLC display subsequently switches at an applied pulse field strength of 10 $V\mu m^{-1}$ with a pulse width of 190 μs. The effective switching angle of the device is 45 degrees.

This example shows that ferroelectric mixtures which have short response times and favorable effective switching angles in liquid-crystal cells can be prepared using the component according to the invention.

We claim:

1. A bispyrimidinylcyclohexane derivative of formula (I)

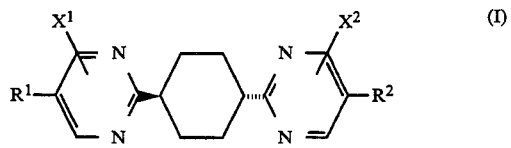

wherein, each of $R^1$ and $R^2$ is a straight-chain or branched (with or without an asymmetric carbon atom) alkyl or alkenyl having 1 to 16 carbon atoms, and $R^1$ may be the same as or different from $R^2$, one or two non-adjacent —$CH_2$— groups replaceable with —O—, —CO—O— or —O—CO— and one or more H replaceable with F, and each of $X^1$ and $X^2$ is H or F, and $X^1$ may be the same as or different from $X^2$.

2. A bispyrimidinylcyclohexane derivative as claimed in claim 1, wherein both radicals $R^1$ and $R^2$ in the formula (I) are linear or branched alkyl or alkoxy groups having 1 to 16 carbon atoms.

3. A bispyrimidinylcyclohexane derivative as claimed in claim 1, wherein $R^1$ and $R^2$ are linear alkyl or alkoxy groups having 1 to 16 carbon atoms.

4. A bispyrimidinylcyclohexane derivative as in claim 1, wherein the derivative is a component of liquid-crystal mixtures.

5. A bispyrimidinylcyclohexane derivative as claimed in claim 4, wherein the liquid-crystal mixture is nematic.

6. A bispyrimidinylcyclohexane derivative as claimed in claim 4, wherein the liquid-crystal mixture is ferroelectric.

7. A liquid-crystalline mixture comprising at least two components, which contains at least one bispyrimidinylcyclohexane compound of the formula (I) as claimed in claim 1.

8. A liquid-crystalline mixture as claimed in claim 7, which contains from 1 to 60 mol% of at least one bispyrimidinylcyclohexane derivative.

9. A liquid-crystal switching and display device containing outer plates, at least one alignment layer, electrodes and a liquid-crystalline medium wherein the liquid-crystalline medium is a mixture as claimed in claim 7.

10. A liquid-crystalline mixture as claimed in claim 7 wherein the mixture is ferroelectric.

* * * * *